(12) United States Patent
Keenan et al.

(10) Patent No.: US 7,649,123 B2
(45) Date of Patent: Jan. 19, 2010

(54) PROPYLENE OLIGOMERIZATION PROCESS

(75) Inventors: Michael J. Keenan, Baton Rouge, LA (US); Ramzi Y. Saleh, Baton Rouge, LA (US); James C. Vartuli, West Chester, PA (US); Robert C. Lemon, Easton, PA (US); Jean W. Beeckman, Columbia, MD (US); Christopher C. Boyer, Houston, TX (US); Mitchell E. Loescher, Houston, TX (US)

(73) Assignees: Catalytic Distillation Technologies, Pasadena, TX (US); ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 12/014,406

(22) Filed: Jan. 15, 2008

(65) Prior Publication Data

US 2009/0182183 A1 Jul. 16, 2009

(51) Int. Cl.
C07C 2/10 (2006.01)
(52) U.S. Cl. ............... 585/530; 585/510; 585/520
(58) Field of Classification Search ......... 585/510, 585/520, 530
See application file for complete search history.

(56) References Cited

U.S. PATENT DOCUMENTS

| 4,215,011 A | 7/1980 | Smith, Jr. |
| 4,242,430 A | 12/1980 | Hara et al. |
| 4,302,356 A | 11/1981 | Smith, Jr. |
| 4,695,664 A | 9/1987 | Whittle |
| 4,731,229 A | 3/1988 | Sperandio et al. |
| 4,873,385 A | 10/1989 | Avidan et al. |
| 4,956,514 A | 9/1990 | Chu |
| 5,073,236 A | 12/1991 | Gelbein et al. |
| 5,113,034 A | 5/1992 | Soled et al. |
| 5,266,546 A | 11/1993 | Hearn |
| 5,431,890 A | 7/1995 | Crossland et al. |
| 5,510,555 A | 4/1996 | Brunelli et al. |
| 5,608,133 A * | 3/1997 | Chang et al. ............... 585/524 |
| 5,730,843 A | 3/1998 | Groten et al. |
| 6,072,093 A | 6/2000 | O'Neill et al. |
| 6,143,942 A | 11/2000 | Verrelst et al. |
| 6,501,001 B2 | 12/2002 | Commereuc et al. |
| 6,583,329 B1 | 6/2003 | Podrebarac |
| 2005/0049448 A1* | 3/2005 | Loescher et al. ........... 585/533 |
| 2007/0123743 A1* | 5/2007 | Ng et al. ................... 585/260 |

OTHER PUBLICATIONS

International Search Report issued in Application No. PCT/US2009/030817 dated Jun. 23, 2009 (3 pages).
Written Opinion issued in Application No. PCT/US2009/030817 dated Jun. 23, 2009 (5 pages).

* cited by examiner

Primary Examiner—In Suk Bullock
(74) Attorney, Agent, or Firm—Osha • Liang LLP

(57) ABSTRACT

A process for the oligomerization of propylene is disclosed wherein a tungstated zirconia catalyst prepared as a distillation structure is used in a reaction distillation zone under conditions of temperature and pressure to concurrently react the propylene to produce oligomers thereof and separate the oligomer products from unreacted propylene by fractional distillation in a distillation column reactor. Compared to the prior art tubular or plug flow reactors, lower temperatures and pressures are used to produce higher conversions and selectivities to preferred isomeric forms useful for preparing neo acids.

15 Claims, 2 Drawing Sheets

PROPYLENE OLIGOMERIZATION PROCESS

BACKGROUND OF DISCLOSURE

1. Field of the Disclosure

Embodiments disclosed herein relate generally to a process for converting propylene over a tungstated zirconia catalyst to provide higher molecular weight hydrocarbons, particularly $C_6$, $C_9$ and $C_{12}$ olefins with high conversion and high selectivity to the $C_6$ and $C_9$ olefins having good branching type isomers for producing neo acids. More particularly the conversion is carried out simultaneously with distillation in a distillation column reactor.

2. Background

In the present state of the art the catalysts are used in tubular reactors at severe conditions, i.e., 330-482° F. and 1000 to 1215 psig pressures. Prior catalysts which have been used for the oligomerization of propylene include supported phosphoric acid (sPa), metal complexes (U.S. Pat. Nos. 5,510,555; 4,695,664 and 6,501,001) and various zeolites, especially ZSM-22 and ZSM-57 (U.S. Pat. No. 6,143,942). These reaction systems have undesirable qualities characterized as one or more of: severe reaction conditions, short catalyst life and poor selectivity.

The reaction requires high temperature (330-482° F.) and high pressure (1000 to 1215 psig). The sPa system has a life of less than 1000 tons of product per ton of catalyst and then must be removed and discarded. The zeolites have shown increased life, e.g., 1500 to 3000 tons product per ton of catalyst, but lose activity and must be regenerated at considerable expense. U.S. Pat. No. 6,072,093 teaches that the catalyst life may be extended by recycling cycloparaffins through the tubular reactor, which requires additional separation and recycling apparatus and an inventory of the non associated cycloparaffins. The metal complexes are homogeneous catalysts wherein the catalyst and the products must be separated with continuous catalyst makeup required. The selectivity of the sPa is toward the $C_9$ and heavier while the preferred oligomers are the $C_6$ and $C_9$ which are converted to alcohols. The selectivities of the zeolites and metal complexes are somewhat better.

U.S. Pat. No. 4,956,514 discloses zeolite MCM-22 which has been shown to have favorable characteristics for the oligomerization of propylene at lower pressures and temperatures than the other catalyst.

U.S. Pat. No. 4,242,430 discloses the dimerization of isobutylene in a distillation column reactor using an acidic cation exchange resin as the catalyst which avoided the formation of higher oligomers.

U.S. Pat. Nos. 5,113,034 and 5,608,133 disclose that tungsten/zirconia catalysts may be used in fixed bed tubular reactors to dimerize $C_3$ and $C_4$ olefins.

SUMMARY OF THE DISCLOSURE

In one aspect, embodiments disclosed herein relate to a process for the oligomerization of propylene comprising: contacting propylene with a tungstated zirconia catalyst in a reaction distillation zone under conditions of temperature and pressure to concurrently react the propylene to produce oligomers thereof and separate the oligomer products from unreacted propylene by fractional distillation.

It has been found that the oligomerization of propylene over tungstated zirconia in a distillation column reactor may be carried out at lower temperatures, below 300° F., preferably less than 200° F., and pressures below about 500 psig, than in the prior art tubular reactors to produce a higher conversion to more desirable oligomeric isomer forms. The conditions for the present reaction are much less severe than that required by earlier zeolite oligomerization processes.

The distillation column reactor preferably operates at a pressure in the range from about 200 to 450 psig, such as about 400 psig, and temperatures in the range of about 140 to 200° F., such as between 140° F. and 165° F. In a family of embodiments, the temperature may be in the range from about 143 to 147° F.; from about 158° to 165° F. in yet other embodiments. Conversions of about 70 to 75% have been achieved yielding about 30% hexene and 40% nonene. The branched type of product is particularly suited for producing neoacids.

As used herein the term "distillation column reactor" means a distillation column which also contains catalyst such that reaction and distillation are going on concurrently in the column. In a preferred embodiment the tungstated zirconia catalyst is prepared as a distillation structure and serves as both the catalyst support and distillation structure.

Other aspects and advantages will be apparent from the following description and the appended claims.

DETAILED DESCRIPTION

Figure 1:
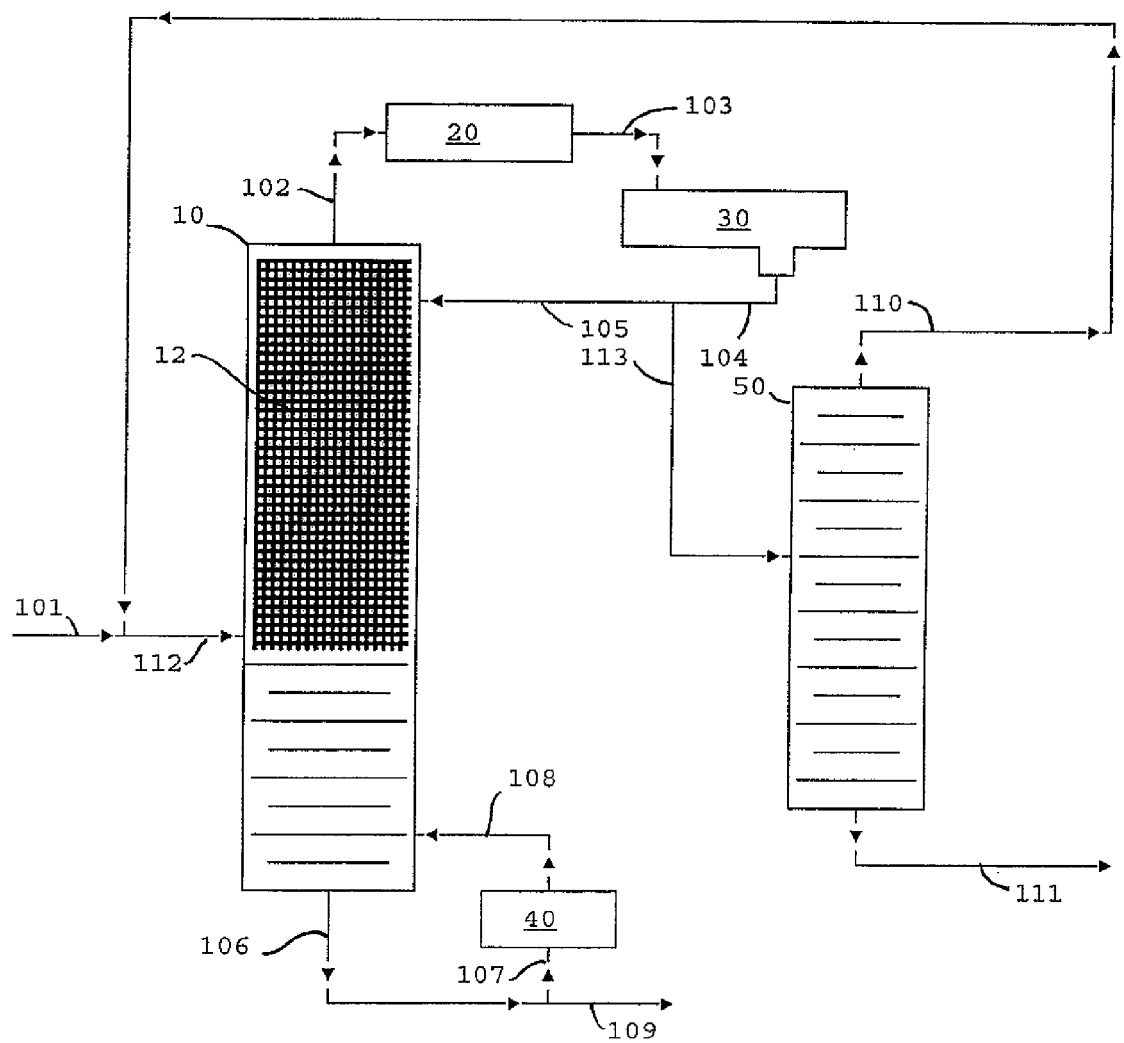
FIG. 1 is a simplified flow diagram of the invention with the distillation column reactor operated in the up flow mode.

The normal feed for the oligomerization is a $C_3$ cut, which contains 20 to 100 mole % propylene. The balance is predominately propane, with minor amounts of ethylene, ethane and the lighter $C_4$'s.

The column may be operated in up flow mode or down flow mode. In up flow mode, the feed (propane and propylene) is placed below the catalyst bed. The reactants are boiled up into the catalyst where they react and the heavier oligomer product is removed out the bottom of the distillation column reactor. Unreacted propylene and inert propane are removed for the top of the distillation column reactor and may be recycled back into the reactor after adjusting for the propane/propylene content.

In down flow mode the column is operated such that the feed (propane and propylene) enters the top of the column, while oligomer product and inert propane are removed from the bottom of the distillation column reactor. The reactive component, propylene, is the lighter component and becomes concentrated in the top of the column by distillation. The catalyst bed is placed in the top of the column where the propylene concentration bulges. Overhead distillate flow may be minimized such that the propylene is refluxed to exhaustion.

Catalyst life is improved when using the tungstated zirconia catalyst as packing in a distillation column reactor. The unique hydraulic action in a distillation column washes out the heavy oligomers as they are produced and prevents fouling. Tungstated zirconia catalyst is described in detail in U.S. Pat. No. 4,956,514 which is incorporated herein.

In accordance with the present invention, anion modified zirconium are impregnated with a tungstate precursor to form the catalyst used in the present invention. Suitable sources of the oxide include salt solutions, such as zirconium oxychlorides, nitrates and tetrachlorides. The salt solution is preferably water soluble and capable of forming a hydroxide precipitate upon the addition of a base. Suitable bases include, but are not limited to ammonium hydroxide and alkylammonium hydroxide, which are added in order to adjust the pH of the solution in the range from about 9 to about 11, thereby facilitating the formation of the hydroxide precipitate. Alkoxides may also be employed for preparing the catalyst, e.g., zirconium propoxide which is hydrolyzed with water to form the hydroxide precipitate.

Any material capable of forming tungstate when calcined with the zirconia oxide may be used to provide the tungstate, such as ammonium meta-tungstate.

The anion can be incorporated with the hydroxide or oxide by any one of several known methods. For example, a zirconium hydroxide or oxide can be immersed in an aqueous solution containing the tungstate followed by drying at about 100° C. to 150° C. After the tungstate source has been incorporated with the zirconium hydroxide or oxide and dried, calcination is carried out, preferably in an oxidizing atmosphere or one that will allow conversion to the tungstate, at temperatures of about 450° C. to about 800° C., preferably about 500° C. to about 600° C. for about 0.5-30 hours, preferably about 1-24 hours. In the most preferred embodiment calcination is carried out at about 600EC for about 0.5 to about 10 hours in air. The concentration of the tungstate remaining on the catalyst after calcination preferably ranges for about 3.0 wt % to about 5 wt % based on the weight of the zirconia metal oxide.

Alternatively, the hydroxide can first be calcined at temperatures ranging from 450° C. to 650° C. to convert the hydroxide, the tungstate being incorporated as previously mentioned.

The supported catalyst may be formed by heating at 60° C. to 90° C. a water slurry of silica added to an aqueous solution of zirconium oxynitrate and urea. The zirconium salt deposits on the silica and is then dried and calcined as previously mentioned. Catalyst loading for supported catalyst may range from about 1% to 25% by weight of catalyst.

The tungstated zirconia catalyst, as provided, is much too fine to function as catalytic distillation structures in a distillation column reactor as required by the present invention. The catalytic distillation structure must be able to function as catalyst and as mass transfer medium. The catalyst is preferably supported and spaced within the column to act as a catalytic distillation structure. The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in a combination reactor-distillation structures. Catalytic distillation structures useful for this purpose are disclosed in U.S. Pat. Nos. 4,731,229, 5,073,236, 5,431,890, 5,266,546 and 5,730,843 which are incorporated by reference. A preferred catalytic distillation structure embodiment is described in U.S. Pat. No. 5,431,890.

Referring now to FIG. 1, the operation of the distillation column reactor in the up flow mode is shown. Fresh feed which includes propylene in flow line 101 is combined with recycle from flow line 110 in flow line 112 and fed to distillation column reactor 10 below a bed 12 of tungstated zirconia catalyst prepared as a distillation structure. The reactants are boiled up into the bed where the propylene reacts with itself and dimers of itself to produce the oligomer products, mainly $C_6$, $C_9$ and $C_{12}$ oligomers. The oligomer products, being higher boiling, are removed from the distillation column reactor as bottoms via flow line 106. A portion of the bottoms are cycled through reboiler 40 via flow lines 107 and 108, and the remainder of the bottoms is recovered via flow line 109. Unreacted propylene and inert propane are removed from the distillation column reactor 10 as overheads via flow line 102, condensed in condenser 20 and collected in receiver 30. The condensed liquid is removed from the receiver 30 via flow line 104 with a portion being returned to distillation column 10 as reflux via flow line 105. The remainder of the liquid distillate is passed via flow line 113 to distillation column 50 where the propane is separated from the mixture and removed as bottoms via flow line 111. The propylene, along with some propane, is taken as overheads and may be recycled to distillation column reactor 10 via flow line 110.

Figure 2:
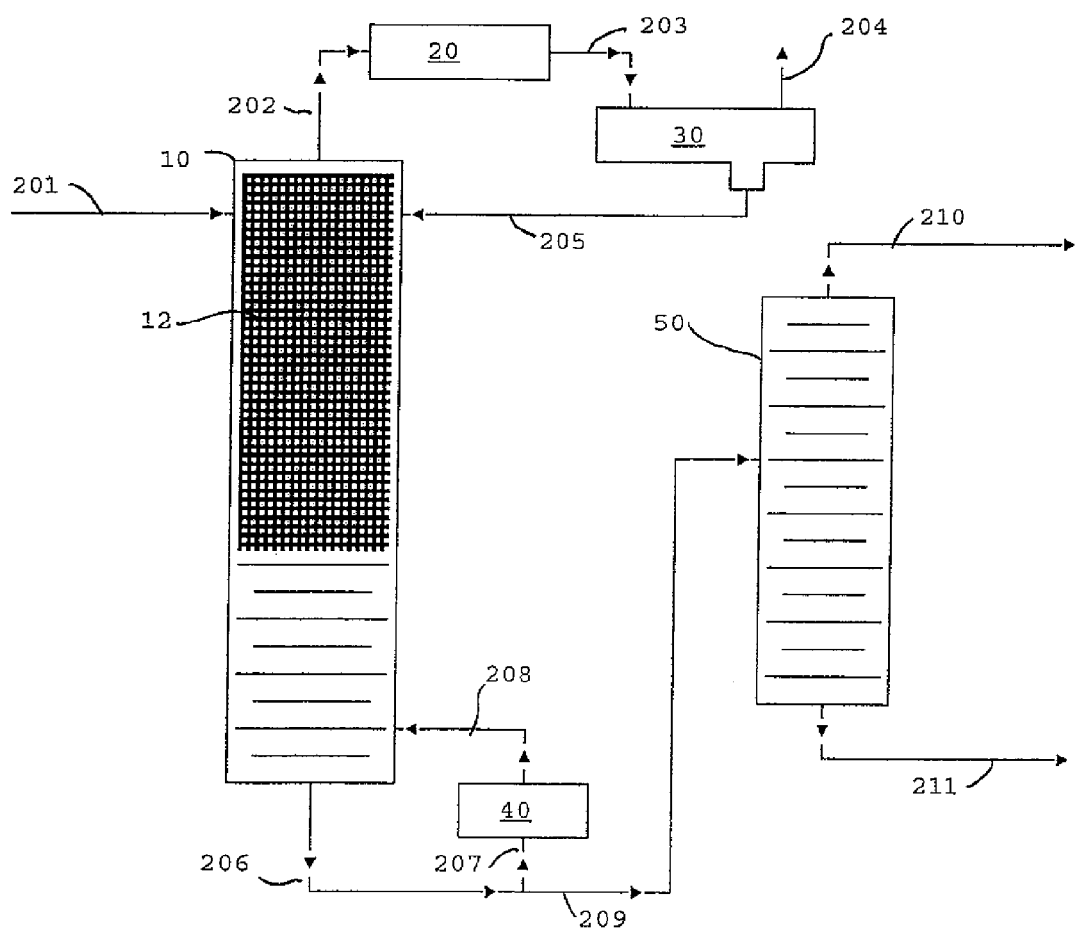
FIG. 2 is a simplified flow diagram of the invention with the distillation column reactor operated in the down flow mode.

Referring now to FIG. 2, the operation of the distillation column reactor in the down flow mode is shown. Feed containing propylene in flow line 201 is fed to the top of the distillation column 10 having a bed 12 of the tungstated zirconia catalyst prepared as a distillation structure. The reactive propylene is the lighter component and is concentrated in the upper part of the column containing the tungstated zirconia catalyst. Some unreacted propylene is taken as overheads via flow line 202, condensed in condenser 20 and thence to receiver 30 via flow line 203 where all of the liquid is returned as reflux to the column 10 via flow line 205 assuring essentially complete conversion. A purge via flow line 204 is provided to prevent build up. The propylene reacts with itself and dimers of itself in the catalyst bed 12 to produce the desired oligomer product, mostly $C_6$, $C_9$ and $C_{12}$ oligomers. The oligomer product and inert propane are removed as bottoms from the distillation column reactor 10 via flow line 206, of which a portion may be fed via flow line 207 to reboiler 40 and thence returned to column 10 via flow line 208. The remaining portion of the bottoms may be fed to distillation column 50 via flow line 209 where the propane is separated as overheads via flow line 210 from the oligomer product which is taken as bottoms via flow line 211.

As used herein the description "feeding at the top of the bed" includes feed above the catalyst bed and the description "feeding at the bottom of the bed" includes feed below the catalyst bed.

TABLE I below presents comparative data showing results using various processes including the present invention. In the MODE section CD=catalytic distillation or the use of a catalytic distillation column.

TABLE I

| | Catalyst | | | |
|---|---|---|---|---|
| | sPa | ZSM-22 | ZSM-27 | WZrO |
| Reactor Mode | Tubular | Tubular | Tubular | CD |
| Propylene Feed | — | — | — | Downflow* |
| Temperature, ° F. | 330-482 | 330-482 | 330-482 | 143-147 |
| Pressure, psig | 1000-1215 | 1000-1215 | 1000-1215 | 400 |
| Catalyst Life (tons/ton) | <1000 | 1500-2000 | 2000-3000 | To Be Determined |
| Conversion, wt. % | — | — | — | 70 |
| Selectivity, wt. % | | | | |
| $C_6$ | 4 | 36 | 3.5 | 31.3 |
| $C_7$ | 5 | <1 | 2 | 2.3 |
| $C_8$ | 9 | <1 | 2.5 | 0.0 |
| $C_9$ | 52 | 36 | 71 | 38.9 |
| $C_{10/11}$ | 10 | 1.5 | 1.5 | 2.1 |
| $C_{12}$ | 15 | 17 | 13 | 15.2 |
| $C_{12+}$ | 4 | 6 | 6 | 10.2 |

*Downflow = fed at the top of the catalyst bed

The skeletal arrangement of the oligomer affects the reactions that the oligomers can undergo. There are five types of branching about the double bond: Type I (vinyl) is bad and Type II (1,2-disubstituted) is undesirable for producing neoacids. Type III (vinylidene) and Type IV (tri-substituted) are good and Type V (tetra-substituted) is the best for producing neoacids. As shown below in TABLE II the tungstated zirconia (WZrO) catalyst produced more skeletal typed in the hexene product which are particularly suited for producing neoacids, a primary use of oligomer olefins.

TABLE II

| | Catalyst | | | |
|---|---|---|---|---|
| | sPa | ZSM-22 | ZSM-27 | WZrO |
| Reactor Mode | Tubular | Tubular | Tubular | CD |
| Branching Type (Hexenes) | | | | |
| Type I | 1.3 | 2.4 | NA | 6.17 |
| Type II | 19.4 | 17.6 | NA | 33.4 |
| Type III | 6.7 | 10.1 | NA | 7.16 |
| Type IV | 39.4 | 61.2 | NA | 33.5 |
| Type V | 5.6 | 0.6 | NA | 17.1 |

In the nonene product the tungstated zirconia catalyst again produced more skeletal types suitable for neoacid production. See TABLE III below.

TABLE III

| | Catalyst | | | |
|---|---|---|---|---|
| | sPa | ZSM-22 | ZSM-27 | WZrO |
| Reactor Mode | Tubular | Tubular | Tubular | CD |
| Branching Type (Nonenes) | | | | |
| Type I | 1.7 | 2.0 | 1.0 | 5.6 |
| Type II | 14.2 | 19.8 | 13.9 | 21.0 |
| Type III | 8.2 | 7.6 | 7.2 | 14.5 |
| Type IV | 64.2 | 61.1 | 56.7 | 36.2 |
| Type V | 11.8 | 10.4 | 21.2 | 22.8 |

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the oligomerization of propylene, the process comprising:
    contacting propylene with tungstated zirconia catalyst prepared as a distillation structure in a reaction distillation zone under conditions of temperature and pressure to concurrently:
        react the propylene to produce oligomers thereof;
        separate the oligomer products from unreacted propylene by fractional distillations
    wherein a conversion of propylene is at least 70 wt. %;
    wherein a selectivity to $C_6$ and $C_9$ oligomers is at least 70%; and
    wherein the $C_6$ and $C_9$ oligomers consist of an isomeric mixture having at least 57% type III, type IV, and type V branching.

2. A process for the oligomerization of propylene comprising the steps of:
    (a) feeding a stream containing propylene to a distillation column reactor containing a bed of tungstated zirconia catalyst prepared as a distillation structure; and
    (b) concurrently in said distillation column reactor at a pressure below about 500 psig:
        (i) reacting the propylene to produce oligomers thereof, and
        (ii) separating the oligomer products from unreacted propylene by fractional distillations
    wherein a conversion of propylene is at least 70 wt. %;
    wherein a selectivity to $C_6$ and $C_9$ oligomers is at least 70%; and
    wherein the $C_6$ and $C_9$ oligomers consist of an isomeric mixture having at least 57% type III, type IV, and type V branching.

3. The process according to claim 2, wherein said bed of tungstated zirconia catalyst is contained within the upper half of said distillation column reactor.

4. The process according to claim 3, wherein said stream containing propylene is fed to the top of said bed of tungstated zirconia catalyst.

5. The process according to claim 4, wherein said overheads is condensed and substantially all of said overheads is returned to said distillation column reactor as reflux.

6. The process according to claim 3, wherein said stream containing propylene is fed at the bottom of said bed of tungstated zirconia catalyst.

7. The process according to claim 3, wherein said stream containing propylene also contains propane.

8. The process according to claim 7, wherein said stream containing propylene is fed above said bed of tungstated zirconia catalyst.

9. The process according to claim 8, wherein propane is removed in said bottoms along with oligomer products and said bottoms is fed to a distillation column where said propane is separated from said oligomer products.

10. The process according to claim 7, wherein said stream containing propylene is fed below said bed of tungstated zirconia catalyst.

11. The process according to claim 10, wherein propane is removed in said overheads along with unreacted propylene and said overheads are fed to a distillation column where propane is separated from propylene.

12. The process according to claim 2, comprising:
    (c) withdrawing oligomer products from said distillation column reactor as bottoms; and
    (d) withdrawing unreacted propylene from said distillation column reactor as overheads.

13. The process according to claim 12, wherein:
    said stream containing propylene and propane is fed to said distillation column reactor at a point above said bed; and
    said oligomer products and propane are removed from said distillation column reactor as bottoms;
    the process further comprising:
    (e) condensing said overheads and returning substantially all of said condensed overheads to said distillation column reactor as reflux; and
    (f) feeding said bottoms to a distillation column where oligomer products are separated as a second bottoms from propane as a second overheads.

14. The process according to claim 12 wherein:
    said stream containing propylene and propane is fed to said distillation column reactor at a point below said bed;
    said overheads contain unreacted propylene and propane;
    the process further comprising
    (e) condensing said overheads and returning a portion of said condensed overheads to said distillation column reactor as reflux;
    (f) feeding a remainder of said overheads to a distillation column where propane is separated as a second bottoms from propylene as a second overheads; and
    (g) returning said second overheads to said distillation column reactor as feed.

15. The process according to claim 8 wherein the temperature within said bed is between 140° F. and 165° F. and the overhead pressure of said distillation column reactor is in the range of 200-450 psig.

* * * * *

UNITED STATES PATENT AND TRADEMARK OFFICE
CERTIFICATE OF CORRECTION

PATENT NO. : 7,649,123 B2
APPLICATION NO. : 12/014406
DATED : January 19, 2010
INVENTOR(S) : Michael J. Keenan et al.

It is certified that error appears in the above-identified patent and that said Letters Patent is hereby corrected as shown below:

In Claim 1, in line 9, in column 5, it reads "distillations" and should read -- distillation; --.

In Claim 2, in line 11, in column 5, it reads "distillations" and should read -- distillation; --.

Signed and Sealed this

Twenty-third Day of March, 2010

David J. Kappos
*Director of the United States Patent and Trademark Office*